(12) United States Patent
Greer

(10) Patent No.: US 10,699,809 B2
(45) Date of Patent: *Jun. 30, 2020

(54) APPLICATION TO WORKER COMMUNICATION INTERFACE

(71) Applicant: CERNER INNOVATION, INC., Kansas City, KS (US)

(72) Inventor: Richard S. Greer, Roswell, GA (US)

(73) Assignee: CERNER INNOVATION, INC., Kansas City, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/219,523

(22) Filed: Dec. 13, 2018

(65) Prior Publication Data

US 2019/0115101 A1   Apr. 18, 2019

Related U.S. Application Data

(63) Continuation of application No. 15/686,886, filed on Aug. 25, 2017, now Pat. No. 10,210,953, which is a (Continued)

(51) Int. Cl.
*G16H 40/20* (2018.01)
*G16Z 99/00* (2019.01)
(Continued)

(52) U.S. Cl.
CPC .............. *G16H 40/20* (2018.01); *G06F 19/00* (2013.01); *G16Z 99/00* (2019.02); *G16H 10/60* (2018.01)

(58) Field of Classification Search
CPC ............... G06F 19/327; G06F 19/3418; G06F 19/3412; G06F 19/3406; G06F 19/345;
(Continued)

(56) References Cited

U.S. PATENT DOCUMENTS 5,617,471 A   4/1997 Rogers et al.
5,673,308 A   9/1997 Akhavan
(Continued)

OTHER PUBLICATIONS

Final Office Action received for U.S. Appl. No. 11/778,733 dated Jan. 20, 2017, 7 pages.
(Continued)

*Primary Examiner* — Reginald R Reyes
(74) *Attorney, Agent, or Firm* — Shook, Hardy & Bacon L.L.P.

(57) ABSTRACT

A substantially real-time voice, text, and messaging communications system employs application triggers for communications. A system provides communication between an executable application and a worker. The system comprises at least one repository including mapping information associating predetermined indicators conveyed by transaction messages with tasks performed by corresponding workers and communication routing information for use in establishing communication with the corresponding workers. A filter automatically accesses transaction messages processed by an executable application and uses the mapping information to identify a predetermined indicator in a received transaction message and a particular worker associated with the received transaction message. A communication interface generates voice message data representing a voice message for communication to the particular worker in response to identifying the predetermined indicator in the received transaction message and uses the routing information to wirelessly communicate the voice message data to a voice message reproduction device borne by the particular worker. The voice message conveys information concerning content of the received transaction message.

20 Claims, 2 Drawing Sheets

Related U.S. Application Data continuation of application No. 11/778,733, filed on Jul. 17, 2007, now Pat. No. 9,779,209.

(60) Provisional application No. 60/820,120, filed on Jul. 24, 2006.

(51) Int. Cl.
*G06F 19/00* (2018.01)
*G16H 10/60* (2018.01)

(58) Field of Classification Search
CPC ....... A61B 5/002; A61B 5/1115; A61B 5/024; A61B 5/746; G08B 5/22
See application file for complete search history.

(56) References Cited

U.S. PATENT DOCUMENTS

| | | | |
|---|---|---|---|
| 5,802,477 A | 9/1998 | Mizokami et al. | |
| 5,960,404 A * | 9/1999 | Chaar | G06F 9/5038 |
| | | | 705/7.26 |
| 6,151,619 A | 11/2000 | Riddle | |
| 6,233,325 B1 | 5/2001 | Frech et al. | |
| 6,374,102 B1 | 4/2002 | Brachman et al. | |
| 6,564,049 B1 | 5/2003 | Dailey | |
| 6,581,035 B1 | 6/2003 | Madan et al. | |
| 6,628,765 B1 | 9/2003 | Bangs et al. | |
| 6,901,255 B2 | 5/2005 | Shostak | |
| 7,184,527 B1 | 2/2007 | Lin et al. | |
| 2002/0002609 A1 | 1/2002 | Chung et al. | |
| 2003/0005464 A1* | 1/2003 | Gropper | G06F 19/321 |
| | | | 725/115 |
| 2003/0023748 A1 | 1/2003 | Takemoto et al. | |
| 2003/0200226 A1 | 10/2003 | Wells et al. | |
| 2004/0198328 A1 | 10/2004 | Brandenberger | |
| 2004/0198354 A1 | 10/2004 | Pettine, Jr. | |
| 2005/0130639 A1 | 6/2005 | Smith | |
| 2005/0170863 A1 | 8/2005 | Shostak | |
| 2005/0204030 A1 | 9/2005 | Koch et al. | |
| 2006/0049936 A1* | 3/2006 | Collins, Jr. | A61B 5/1115 |
| | | | 340/539.11 |
| 2006/0167738 A1 | 7/2006 | Spear et al. | |
| 2007/0004971 A1 | 1/2007 | Riley et al. | |
| 2008/0021709 A1 | 1/2008 | Greer | |
| 2008/0103720 A1* | 5/2008 | White | G16H 80/00 |
| | | | 702/127 |
| 2017/0357758 A1 | 12/2017 | Greer | |

OTHER PUBLICATIONS

Final Office Action received for U.S. Appl. No. 11/778,733, dated Mar. 14, 2011, 9 pages.

First Action Interview Office Action received for U.S. Appl. No. 15/686,886, dated Mar. 12, 2018, 6 pages.

Non Final Office Action received for U.S. Appl. No. 11/778,733, dated Jul. 25, 2016, 19 Pages.

Non-Final Office Action received for U.S. Appl. No. 11/778,733, dated Jan. 15, 2016, 6 pages.

Non-Final Office Action received for U.S. Appl. No. 11/778,733, dated Sep. 15, 2011, 10 pages.

Non-Final Office Action received for U.S. Appl. No. 11/778,733, dated Sep. 27, 2010, 8 pages.

Non-Final Office Action received for U.S. Appl. No. 15/686,886, dated Nov. 15, 2017, 15 Pages.

Notice of Allowance received for U.S. Appl. No. 11/778,733, dated May 31, 2017, 27 pages.

Notice of Allowance received for U.S. Appl. No. 15/686,886, dated Oct. 2, 2018, 9 pages.

Preinterview First Office Action received for U.S. Appl. No. 15/686,886 dated Dec. 4, 2017, 3 pages.

* cited by examiner

APPLICATION TO WORKER COMMUNICATION INTERFACE

CROSS REFERENCE TO RELATED APPLICATIONS

This application is a continuation of U.S. application Ser. No. 15/686,886, entitled "An Application to Worker Communication Interface" and filed on 25 Aug. 2017, which is a continuation of U.S. Pat. No. 9,779,209, entitled "An Application to Worker Communication Interface" and filed on 17 Jul. 2007, which is a non-provisional of the provisional U.S. App. No. 60/820,120, entitled "An Application to Worker Communication Interface" and filed 24 Jul. 2006, wherein the entirety of these applications being incorporated by reference herein.

FIELD OF THE INVENTION

This invention concerns a system providing communication between an executable application and a worker involving generating voice message data for communication to a worker in response to processing transaction messages.

BACKGROUND OF THE INVENTION

Known systems lack efficiency in their workflow processes in the use of computers for retrieving and managing information. A workflow process comprises a sequence of tasks or steps for performance by a device and/or worker, for example. Known systems involve expenditure of valuable time by a user in getting to and accessing a PC, logging in to an application, and retrieving information concerning a task to be performed in a particular workflow. Repeated trips by a worker to a PC to check on availability of information are typically required involving wasted time. A system according to invention principle addresses these deficiencies and related problems.

SUMMARY OF THE INVENTION

A Voice Application Integration Filter (VAIF) operates with an inter-computer data exchange system and programmatic mapping scheme to automatically communicate a variety of information to user-worn wireless communication badge devices, without manual intervention, in response to embedded application triggers, for example. A system provides communication between an executable application and a worker. The system comprises at least one repository, including mapping information associating predetermined indicators conveyed by transaction messages with tasks performed by corresponding workers and with communication routing information for use in establishing communication with the corresponding workers. A filter automatically accesses transaction messages processed by an executable application and uses the mapping information to identify a predetermined indicator in a received transaction message and a particular worker associated with the received transaction message. A communication interface generates voice message data representing a voice message for communication to the particular worker in response to identifying the predetermined indicator in the received transaction message and uses the routing information to wirelessly communicate the voice message data to a voice message reproduction device borne by the particular worker. The voice message conveys information concerning content of the received transaction message.

DETAILED DESCRIPTION OF THE INVENTION

Figure 1:
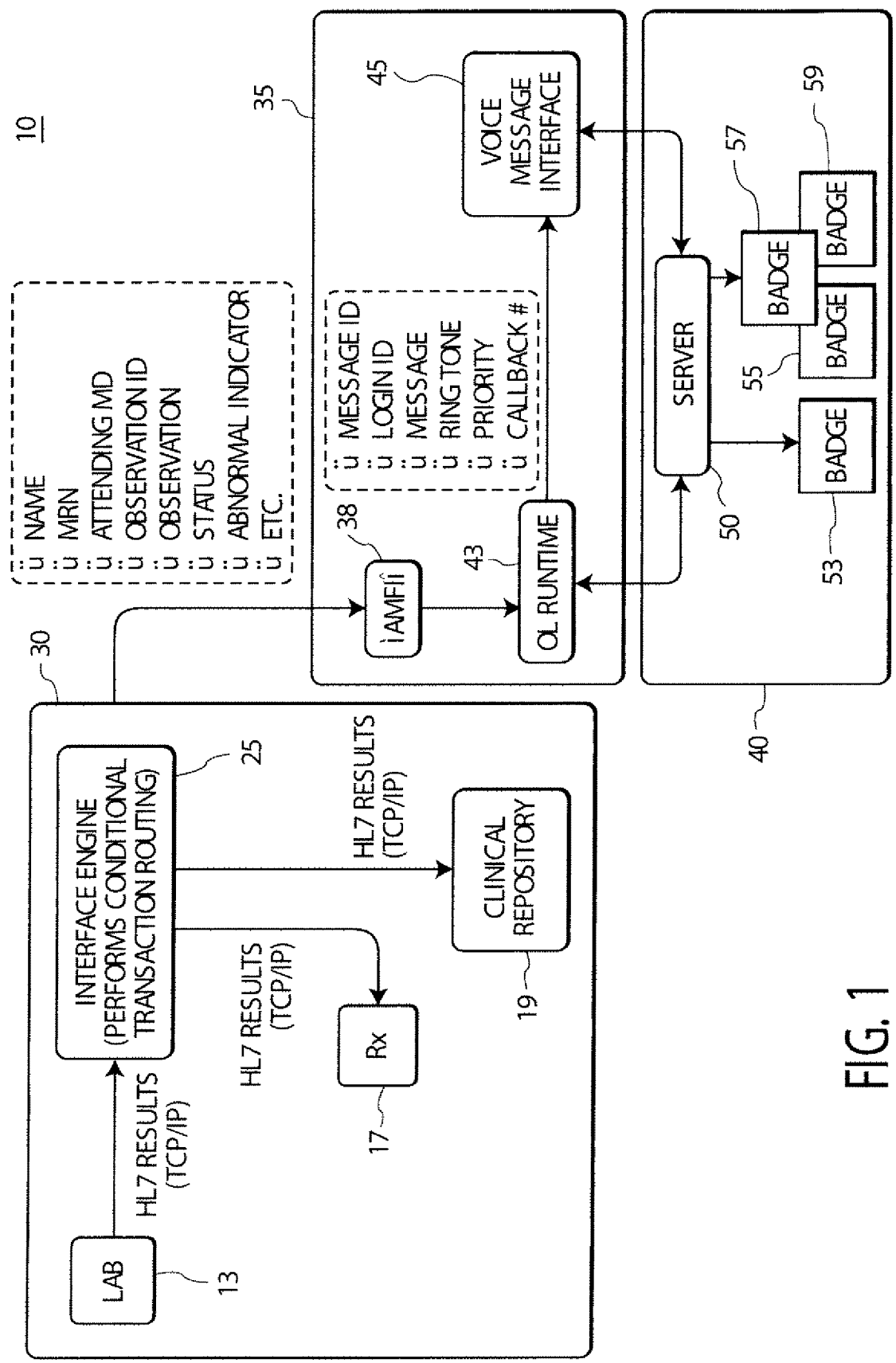
FIG. 1 shows a system providing communication between an executable application and a worker, according to invention principles.

A system provides substantially real-time voice, text, and messaging communications for a mobile, geographically dispersed workforce within a large hospital facility or campus, for example, by employing trigger functions in executable applications. A Voice Application Integration Filter (VAIF) operates with an inter-computer data exchange system and programmatic mapping scheme to automatically communicate a variety of information to user-worn wireless communication badge devices (such as devices compatible with those provided by Vocera) in response to embedded application triggers without manual intervention. The system communicates data identifying treatment orders and results information to clinicians and user-relevant information originating from other healthcare applications such as radiology, respiratory therapy, physical therapy, dietary, transport, housekeeping, and bed management, for example. The system streamlines workflow and improves worker and device productivity.

A processor, as used herein, operates under the control of an executable application to (a) receive information from an input information device, (b) process the information by manipulating, analyzing, modifying, converting, and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of hardware, firmware, and/or software.

An executable application, as used herein, comprises code or machine-readable instructions for conditioning the processor to implement predetermined functions, such as those of an operating system, a context data acquisition system, or other information processing system, for example, in response to user command or input. An executable procedure is a segment of code or machine-readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touchscreen, or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions, or a combination of both, or an executable procedure.

A workflow processor, as used herein, processes data to determine tasks to add to a task list, remove from a task list, or modify tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and/or worker and for updating task lists of a device and/or worker to include determined tasks. A process definition is definable by a user and comprises a sequence of process steps including one or more of start, wait, decision, and task allocation steps for performance by a device and/or worker, for example. An event is an occurrence, affecting operation of a process implemented using a process definition.

A Workflow Management System is a software system that manages processes. It includes a process definition function that allows users to define a process that should be followed, and an Event Monitor, which captures events from a Healthcare Information System and communicates the results to the Workflow Management System. A processor in the Workflow Management System tracks which processes are running, for which patients, and what step needs to be executed next, according to a process definition. The Workflow Management System includes a procedure for notifying clinicians of a task to be performed, through their worklists, and a procedure for allocating and assigning tasks to specific users or specific teams. A document or record comprises a compilation of data in electronic form and is the equivalent of a paper document and may comprise a single, self-contained unit of information.

FIG. 1 shows system 10 providing communication between an executable application and a worker. System 10 employs multiple components including a communication system, Voice Messaging interface (VMI) (e.g., available from Vocera and others), and a data exchange system for exchanging data between different computer systems using different data formats and communication protocols. System 10 includes a filter for capturing and parsing transaction messages such as messages compatible with the Health-Level7 (HL7) standard compatible format from a source application to extract and acquire data items. HL7 is a standard for the exchange, management, and integration of data that supports clinical patient care, and the management and delivery of healthcare services by defining the protocol for exchanging clinical data between diverse healthcare information systems. The filter provides relevant data items for communication to a particular workflow, device, clinician, or worker that needs to take action. The acquired data items are sent to a wireless communication badge device (e.g., such as one available from Vocera and others) after being translated from text to speech by the VMI. Predefined triggers associated with a particular workflow are employed by system 10 to provide a seamless and efficient workflow for healthcare workers, for example. Information relevant to worker-specific tasks is sent automatically to the specific worker wireless communication badge device.

System 10 provides communication between an executable application and a worker using a clinical event interface 30 including a data exchange system 25. System 25 exchanges data between different computer systems (and associated executable applications) including voice messaging interface 35 and voice messaging system 40 using different data formats and communication protocols. Interface 30 also includes a workflow processor including a workflow engine for managing scheduling of performance of tasks by devices and personnel in a hospital, for example, by managing addition, deletion, and amendment of tasks on worklists of devices and personnel. The workflow engine initiates performance of workflows in response to predetermined workflow process definitions stored in a repository in unit 30. The workflow engine uses voice messaging interface 35 and voice messaging system 40 to inform personnel of tasks for performance. Clinical event interface 30 includes at least one repository incorporating mapping information associating predetermined indicators conveyed by transaction messages with tasks performed by corresponding workers and communication routing information for use in establishing communication with the corresponding workers. Filter 38 automatically accesses transaction messages processed by an executable application and uses the mapping information to identify a predetermined indicator in a received transaction message and a particular worker associated with the received transaction message.

The transaction messages that are provided by laboratory information system 13 are communicated to pharmacy system 17 and clinical information repository system 19, and filter unit 38 via data exchange system 25. Transaction messages are also acquired from a variety of other systems (not shown to preserve drawing clarity) including a computerized order entry (CPOE) system, scheduling system, appointment system, treatment management system, admission, discharge and transfer (ADT) system, and a clinical information processing system. The acquired transaction messages are communicated to destination systems via data exchange system 25. A communication interface in voice messaging system 40 generates voice message data representing a voice message for communication to the particular worker in response to identifying the predetermined indicator in the received transaction message. The communication interface uses the routing information to wirelessly communicate the voice message data to a voice message reproduction device borne by the particular worker. The voice message conveys information concerning content of the received transaction message.

In operation, an HL7 compatible transaction message (e.g., conveying laboratory test results) is communicated from laboratory information system 13 to data exchange system 25 using an IP/TCPIP compatible communication protocol in a hospital, for example. System 25 identifies an HL7 message based on predetermined indicators found in an HL7 message (or other format message) header or content. Data exchange system 25 routes the received transaction message to application message filter interface (AMFI) 38 as well as to pharmacy information system 17 and clinical information repository system 19. Data exchange system 25 replicates the transaction message data and sends the replicated transaction message data to a destination system and AMFI 38. The transaction message may, for example, comprise critical laboratory test results and contain data fields conveying patient name and identifier, medical record number, attending physician identifier, test result (observation) identifier, the observation result, status of the result (e.g., final, preliminary, first stage, etc.), an abnormal indicator identifying an observation as abnormal, and other items.

AMFI 38 parses the received transaction message and compares transaction message data elements with predetermined stored alert message generation criteria. The alert message generation criteria stored in a repository in voice messaging interface 35 associates particular HL7 message data elements with particular workflows and alert message destinations (e.g., workers). Specifically, the alert message generation criteria associates identifiers of workers with HL7 message data elements including patient name and identifier, medical record number, attending physician identifier, test result (observation) identifier, and other HL7 conveyed elements. The alert message generation criteria further associate identifiers of workers (such as physicians) with one or more particular workflows (and associated workflow identifiers) as well as one or more particular steps (and associated workflow step identifiers) within a particular workflow.

AMFI 38 parses the received transaction message to identify HL7 message data elements and compares the HL7 message data elements with predetermined stored alert message generation criteria to identify a received transaction message that is associated with a particular physician or destination. Similarly, AMFI 38 may also identify a received transaction message that is associated with one or more other alert generation parameters including patient name and identifier, medical record number, attending physician identifier, test result (observation) identifier, workflow, and step within a workflow. Thereby alert generation criteria act to initiate a request for an information alert message to be generated within a specific workflow, for example. In response to transaction message data matching alert message generation filter criteria, the transaction message is stored in a VMI database in VMI 45 for processing. The processing includes identifying a field in a transaction message, for example the attending MD field. In exemplary operation, messages that are received with an abnormal indicator flag set, along with the attending MD field, are sent to VMI 45 and from there to a wireless communication badge device that the attending MD is wearing, in response to an alert generation criteria match, for example.

Further, in response to a determination, a received transaction message is associated with one or more alert generation criteria and a particular workflow of a hospital, for example, a trigger is activated to convey a transaction message through AMFI 38 and to virtual message interface (VMI) 45 via online processor 43. Processor 43 communicates with VMI 45 via a VMI Application Programming Interface (API) and, in response to matched alert generation criteria identified by AMR 38, provides message generation data to VMI 45. The message generation data includes a destination identifier (e.g., a physician identifier), a message identifier, login ID, the message, ring tone if applicable, a priority (e.g., stat, emergency), and a callback contact number, for example. Processor 43 provides the message, which may comprise a predetermined message or a message derived by incorporation of transaction message data (e.g., test result values) and identifiers of workers (such as physicians) in a template message, for example. In system 10, if a transaction message meets alert generation criteria of AMFI 38, a second replicated transaction is created for transfer to a wireless communication badge device (e.g., devices 53-59). The second transaction is processed in parallel with the original HL7 transaction, which proceeds on to designated locations 17 and 19. If a transaction message does not meet alert generation criteria of AMFI 38, for example, because the transaction message does not relate to a customer-specified workflow for which an alert generation criteria trigger has been defined, the transaction message proceeds to its intended destination.

VMI 45 in voice messaging system 35, processes message generation data received from AMFI 38 to provide a transaction message in a format compatible with a Voice wireless communication application executing on server 50. VMI 45 communicates with server 50 using a TCP/IP protocol, for example. The server 50 communication application initiates communication of a text message to an appropriate corresponding wireless communication badge device of devices 53, 55, 57, and 59 using an Internet compatible communication protocol, for example. Processor 43 also bidirectionally communicates with server 50 and the communication application executing on server 50 to enable server 50 to acquire data supporting messaging and to enable processor 43 to query server 50 to obtain records of messages communicated and success or failure of the communications, for example. This communication may employ database querying protocols such as SQL, ODBC, or an MS Access compatible query protocol, for example.

In operation of system 10, a respiratory therapist receives a next order in data received via a wireless communication badge device from the server 50 communication application while attending a patient at a hospital location. In contrast, a known system requires the respiratory therapist to walk back to a therapy department location and login to an associated computer application and retrieve the next order from the application. In another example, a clinician receives a message that laboratory test results are available for a particular patient while attending patients with a physician and substantially instantly communicates the results to the physician. Further, in a bed management process, house cleaning services are notified by a bed management application via system 10 when a room is vacant and ready to be cleaned. System 10 improves workflow operation by facilitating direct communication of healthcare applications with a healthcare worker using a process involving a hospital interface engine and AMFI 38 receiving an HL7 (for example) transaction message from a hospital application. In one embodiment, the HL7 transaction message is matched against hospital designated message workflows and if the filtered HL7 transaction message meets hospital alert message generation criteria, a corresponding HL7 transaction message is sent to VMI 45 which forwards a corresponding transaction message to a Voice wireless communication badge device (e.g., badge 53).

Figure 2:
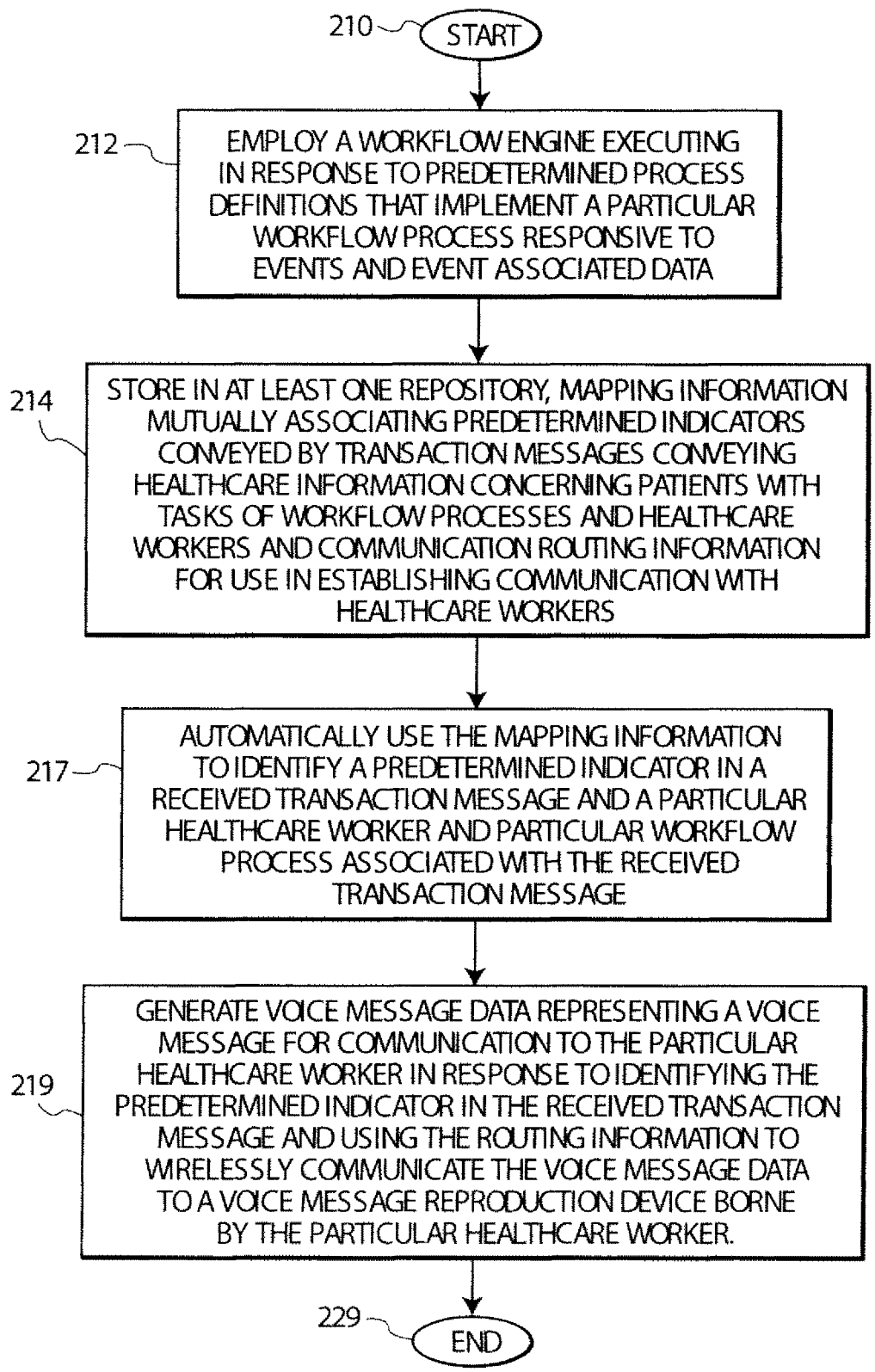
FIG. 2 shows a flowchart of a process performed by a system providing communication between an executable application and a worker, according to invention principles.

FIG. 2 shows a flowchart of a process performed by system 10 providing communication between an executable application and a worker. The steps of FIG. 2 may be performed automatically. In step 212 following the start at step 210, a workflow engine in interface 30 executes in response to predetermined process definitions that implement a particular workflow process responsive to events and event associated data. In another embodiment, a task processor (instead of a workflow engine) in interface 30 manages a particular workflow process responsive to events and event associated data. Interface 30 in step 214 stores in at least one repository in unit 30 (or unit 35) mapping information mutually associating predetermined indicators conveyed by transaction messages conveying healthcare information concerning patients with tasks of workflow processes and with corresponding healthcare workers and with devices performing the tasks as well as with an individual task of a sequence of tasks of the particular workflow and with communication routing information for use in establishing communication between VMI 45 and corresponding healthcare workers and devices. The routing information includes healthcare worker specific communication information indicating one or more of (i) prioritized communication routes and (ii) a callback number. The transaction messages are HL7 (HealthLevel7) protocol compatible messages conveying healthcare information concerning patients.

In step 217, filter 38 automatically accesses transaction messages processed by an executable application in a healthcare organization. Filter 38 automatically, without human intervention, uses the mapping information to identify a predetermined indicator in a received transaction message and a particular healthcare worker and particular workflow process (including individual tasks of a particular workflow) associated with the received transaction message. The mapping information associates a predetermined indicator conveyed by the received transaction message with an individual task of a sequence of tasks of the particular workflow. The predetermined indicators comprise a name, a Medical Record Number (MRN), a Physician identifier or name, a patient identifier, an observation identifier, an encounter identifier, a medical observation, a patient status, and an abnormal patient laboratory result or parameter indicator, for example. Filter 38 identifies fields in the received transaction message incorporating predetermined indicators identifying a physician and an abnormal test result indicator. Filter 38 comprises a conditional routing processor used in routing transaction messages to at least one of (a) laboratory, (b) pharmacy, and (c) a patient medical record in a healthcare organization.

In step 219, communication interface 35 generates voice message data representing a voice message for communication to the particular healthcare worker in response to identifying the predetermined indicator in the received transaction message. The generated voice message data includes a message together with at least one of (a) a message identifier, (b) a login identifier, and (c) a ring tone, for example. Communication interface 35 uses the routing information to wirelessly communicate the voice message data to a voice message reproduction device borne by the particular healthcare worker. The voice message conveys information concerning content of the received transaction message to inform a worker of the individual task of the particular workflow to be performed. Communication interface 35 generates voice message data representing a voice message containing an abnormal test result for communication to a particular healthcare worker, for example. The process of FIG. 2 terminates at step 229.

The system and process of FIGS. 1-2 are not exclusive. Other systems, processes, and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. System 10 is usable in any field employing applications for reporting messages to a user. For example, in Building Technology, an application sends a maintenance message to a worker from a check valve that needs to be serviced, or if an elevator breaks, an error message is sent directly to a service technician wearing a voice badge. On an assembly line when a stock part is in low supply, system 10 notifies a user that stock is low. The processes and applications may, in alternative embodiments, be located on one or more (e.g., distributed) processing devices accessing a network linking the elements of FIG. 1. Further, any of the functions and steps provided in FIGS. 1 and 2 may be implemented in hardware, software, or a combination of both and may reside on one or more processing devices located at any location of a network linking the elements of FIG. 1 or another linked network including the Internet.

What is claimed is:

1. A voice communication badge device comprising:
    a processor that wirelessly receives data including a voice message from a communication interface, the data conveying transaction message information processed by the communication interface, the transaction message information corresponding to an order identified by the communication interface; and
    a speaker that audibly communicates the voice message to a person associated with the device, the voice message informing the person associated with the device to perform the order identified by the communication interface,
    wherein the voice communication badge device is communicatively coupled to the communication interface,
    wherein the data conveying transaction message information is processed by the communication interface by mapping predetermined indicator subcomponents encoded in the data to the order and by identifying the person associated with the device to which the voice message is to be communicated based on mapping the predetermined indicator subcomponents encoded in the data to the order, and
    wherein the voice message is generated by the communication interface, the voice message including the order based on the predetermined indicator subcomponents and encoding a unique message identifier and audio content that includes at least a portion of the transaction message information corresponding to the order.

2. The device of claim 1, wherein the data wirelessly received from the communication interface includes a ringtone, and the speaker audibly communicates the ringtone to the person associated with the device.

3. The device of claim 1, wherein the data wirelessly received from the communication interface includes a login identifier, and the speaker audibly communicates the login identifier to the person associated with the device.

4. The device of claim 1, wherein the data wirelessly received from the communication interface includes a priority for the voice message, and the speaker audibly communicates the priority of the voice message to the person associated with the device.

5. The device of claim 1, wherein the data wirelessly received from the communication interface includes callback contact information, and the speaker audibly communicates the callback contact information to the person associated with the device.

6. A system for generating and communicating voice messages to a wireless badge in real time, the system comprising:

a communication interface having a processor to:
identify subcomponents encoded in a transaction message by parsing the transaction message, the subcomponents comprising predetermined indicators;
identify a recipient for the transaction message and a voice communication badge device corresponding to the recipient, as specified by one or more of the predetermined indicators;
map at least one of the predetermined indicators to a task for an order;
generate a voice message based on the predetermined indicators, the voice message including the task for the order, and the voice message encoding a unique message identifier and audio content that includes at least a portion of the transaction message corresponding to the task for the order; and
communicate the voice message to the voice communication badge device associated with the recipient; and
the voice communication badge device having a processor and a speaker to:
wirelessly receive the voice message generated by the communication interface; and
audibly communicate the voice message to the recipient associated with the voice communication badge device, the voice message informing the recipient to perform the task for the order mapped by the communication interface.

7. The system of claim 6, wherein the communication interface having the processor comprises:
an application message filter interface to receive a plurality of transaction messages, wherein for each of the plurality of transaction messages, the application message filter interface identifies the subcomponents including the predetermined indicators encoded in the plurality of transaction messages by parsing the transaction messages in real time.

8. The system of claim 7, wherein the application message filter interface further:
for each one of the predetermined indicators, identifies one task for the order that is associated with the predetermined indicator.

9. The system of claim 7, wherein the application message filter interface comprises a conditional routing processor to route the plurality of transaction messages to other systems using a data exchange system.

10. The system of claim 6, wherein the communication interface having the processor comprises:
an online runtime processor running an application programming interface for communicating information of the transaction message, including the predetermined indicators, to a virtual message interface.

11. The system of claim 6, wherein the communication interface having the processor comprises:
a virtual message interface that uses recipient-specific routing information obtained from a data repository to communicate the voice message to the voice communication badge device that is associated with the recipient.

12. The system of claim 11, wherein the recipient-specific routing information includes callback contact information.

13. The system of claim 6, wherein the communication interface having the processor comprises:

a repository storing a plurality of orders, each of the plurality of orders comprising one or more tasks for a corresponding order, and storing mapping information that associates each of the one or more tasks with the predetermined indicators.

14. A method for generating and communicating voice messages to voice communication badge devices, the method comprising:
identifying subcomponents encoded in a transaction message by parsing the transaction message, the subcomponents comprising predetermined indicators;
identifying a recipient for the transaction message and a voice communication badge device corresponding to the recipient, as specified by one or more of the predetermined indicators;
mapping at least one of the predetermined indicators to a task corresponding to an order;
generating, by a communication interface, a voice message based on the predetermined indicators, the voice message including the task corresponding to the order, and the voice message encoding a unique message identifier and audio content that includes at least a portion of the transaction message corresponding to the task corresponding to the order; and
communicating the voice message to the voice communication badge device associated with the recipient,
wherein the voice communication badge device associated with the recipient wirelessly receives the voice message generated by the communication interface, and
wherein the voice communication badge device audibly communicates the voice message to the recipient, the voice message informing the recipient to perform the task corresponding to the order, as mapped by the communication interface.

15. The method of claim 14, wherein the method is performed in real time.

16. The method of claim 14, further comprising:
determining whether the predetermined indicators are associated with one or more criteria prior to generating the voice message.

17. The method of claim 16, wherein the one or more criteria comprise an association between the predetermined indicators and the recipient, an association between the task corresponding to the order and the recipient, and an association between one or more tasks corresponding to the order and associated with the recipient.

18. The method of claim 14, wherein generating the voice message based on the predetermined indicators further comprises:
converting one or more of the subcomponents including the predetermined indicators encoded in the transaction message into a format compatible with a voice communication application.

19. The method of claim 14, further comprising:
for each one of the predetermined indicators, identifying one task corresponding to the order that is associated with the predetermined indicator.

20. The method of claim 14, further comprising:
using recipient-specific routing information obtained from a data repository to communicate the voice message to the voice communication badge device that is associated with the recipient.

* * * * *